(12) United States Patent
Haskin et al.

(10) Patent No.: US 7,939,152 B2
(45) Date of Patent: May 10, 2011

(54) HEAT-SHRINKABLE ANTI-FOMITIC DEVICE

(75) Inventors: Marvin E. Haskin, Bryn Mawr, PA (US); Jon L. Roberts, Great Falls, VA (US); Christopher B. Kilner, Oak Hill, VA (US)

(73) Assignee: M-Tech Corporation, Great Falls, VA (US)

( * ) Notice: Subject to any disclaimer, the term of this patent is extended or adjusted under 35 U.S.C. 154(b) by 91 days.

(21) Appl. No.: 12/130,524

(22) Filed: May 30, 2008

(65) Prior Publication Data
US 2008/0296193 A1    Dec. 4, 2008

Related U.S. Application Data

(60) Provisional application No. 60/941,499, filed on Jun. 1, 2007.

(51) Int. Cl.
*B29D 22/00* (2006.01)
*B29D 23/00* (2006.01)
*B32B 1/08* (2006.01)

(52) U.S. Cl. ............... 428/36.91; 428/35.2; 428/35.4; 428/35.7; 428/36.6; 428/36.7

(58) Field of Classification Search ............. 428/35.2, 428/35.4, 35.7, 121, 124, 36.91, 36.6, 36.7; 206/41.7, 200, 438, 455; 383/42, 63, 64, 383/93, 95, 97, 98, 211
See application file for complete search history.

(56) References Cited

U.S. PATENT DOCUMENTS

| | | | | |
|---|---|---|---|---|
| 3,111,449 | A | * | 11/1963 | Gold et al. .............. 428/40.6 |
| 3,917,160 | A | * | 11/1975 | Olerud .................... 383/93 |
| 6,468,611 | B1 | | 10/2002 | Haskin |
| 6,649,236 | B2 | | 11/2003 | Haskin |

* cited by examiner

*Primary Examiner* — Michael C Miggins
(74) *Attorney, Agent, or Firm* — The Marbury Law Group PLLC

(57) ABSTRACT

A heat-shrinkable anti-fomitic device in the form of a bag or tube forms a cover for an object which prevents cross-infection by bacteria and other pathogens that may reside on the object. The heat-shrinkable anti-fomitic device can have a sterile interior that is sealed or stored flat during manufacture to maintain sterility. Therefore, no outer wrapping for the anti-fomitic device is required. The anti-fomitic device is inverted when used to cover the object and results in an ultimate outer surface that is initially sterile. A plurality of such devices can be heat shrunk to an object such that removal of the outer layer will prevent cross contamination. Heat shrink film materials for the coverings/bags serve as a barrier to the transmission of pathogens.

12 Claims, 7 Drawing Sheets

HEAT-SHRINKABLE ANTI-FOMITIC DEVICE

CROSS-REFERENCE TO OTHER INVENTIONS

This application claims the benefit under 35 U.S.C. §119 of the filing date of Provisional Application No. 60/941,499 filed Jun. 1, 2007. The 60/941,499 application is incorporated by reference herein, in its entirety, for all purposes.

BACKGROUND AND SUMMARY

The present invention relates generally to a cover or barrier formed of shrink film to prevent cross-infection. In particular, the present invention relates to a range of anti-fomitic covers to prevent cross-infection, including such covers for pillows, mattresses, X-ray cassettes, surgical and diagnostic equipment, toilet seats, table and chair seat surfaces, wash basin faucet handles and other handles, etc.

As disclosed in one of the present inventors' U.S. Pat. Nos. 6,468,611 and 6,649,236, the problems of cross-infection and the production of antibiotic-resistant mutations have been subjects for concern in hospital settings, as well as in household and other settings, such as the hospitality industry (hotels, motels, bed and breakfast businesses, hostels, etc.). These problems are particularly problematic for those with compromised immune systems or with special bacterial, viral fungal, parasitic, or other susceptibilities. The latter category of special susceptibilities may also include persons with allergies, and persons who develop one or more of a range of contact dermatitises, to name but a few non-limiting examples.

One way that bacteria, viruses, fungi, and other pathogens are transmitted is by fomites, which are inanimate agents of such transmissions, including, for example, bedding, toilet seats, clothes, table tops and other fixed surfaces, surgical and X-ray equipment, computer keyboards, etc. Thus, a fomite (also called a fomes) may absorb or otherwise harbor one or more strains of pathogenic bacteria, fungi, viruses, etc., and later transmit those pathogens, by contact, to a human.

A common fomite found in hospitals is metallic X-ray cassettes. Both patients and hospital staff may handle or otherwise touch an X-ray cassette, depending on the X-ray system used and the particular application. For example, in some applications, an undraped patient may hold an X-ray cassette in position against a portion of his body during X-ray filming. Subsequent to the filming, one or more hospital staff members may also touch the X-ray cassette during the progression culminating in photographic development of the X-ray film.

One study of hospitals (Surgical Clinics of North America 50 [No. 4]: pages 945-952, August 1970) included analysis of portions of X-ray rooms and X-ray equipment, including cassettes used in portable X-ray machines. Organisms cultured from these cassettes included *staphylococcus aureus* (coagulase negative), *staphylococcus aureus* (coagulase positive), *streptococcus viridans*, *aspergillus*, fungus, and diptheroids. The cassettes cultured in this study included ones placed in direct contact with undraped patients.

Another common fomite is bedding, where commonly employed materials, such as cotton, act as wicks to carry pathogens far from the initial contact point with human skin, particularly when moisture is present (sweat, semen, saliva, vaginal secretions, secretions from wounds and open pimples, spilled drinks, etc.). Thus, when sheets and pillow cases are changed, the deeper lying material (mattress, mattress cover, pillow) still harbors potential pathogens of the previous user(s). Furthermore, the next user—particularly when moisture is introduced onto the "scene"—can become infected by reverse wicking; i.e., moisture can draw deep lying pathogens back toward the surface of the bedding that is in contact with the user.

Another common fomite is the surfaces encountered in bathrooms. As has been well documented for decades, toilet seats, the faucet handles of wash basins, door handles, etc., and other surfaces in bathrooms are commonly contaminated with *E. coli* and other pathogens. As but one illustration of the problem, one need only recognize that a user of a toilet often will leave the toilet with substantial *E. coli* contamination of at least one hand. That individual may then, in turn, contaminate the knob/handle of the toilet stall, and then one or more faucet handles at a wash basin. Said individual then washes his hands, but touches the one or more faucet handles that he had just contaminated in the process of turning off the water flow, thereby re-contaminating his hand(s). Thus, whatever is subsequently touched by the *E. coli*-contaminated hand(s) of that individual will also become so contaminated.

As another example of cross-contamination in the bathroom setting, pathogens on toilet seats may be transmittable to the next user. One such example is the herpes viruses, which may be transmitted to a subsequent contactor, particularly if that individual has an open wound. Other pathogens may similarly be so transmitted, though some will require relatively immediate contact by the next person when the pathogen is not hardy outside a "biological" setting (i.e., a setting having the requisite moisture and/or temperature close to human interior body temperature).

Yet another setting that is ripe for cross-contamination is the kitchen. Not only is there the well documented potential problems with contamination sources such as chicken skin (*Salmonella*, etc.), raw beef (*E. coli*, etc.), and insects and other bugs and parts thereof (keeping in mind that the FDA allows such contamination to prescribed levels), but also *E. coli* contamination due to the use of toilets by the kitchen worker (or from contamination by a previous user of the toilet). In the same manner noted above in the context of bathrooms, cross-contamination of faucet handles of wash basins/sinks in kitchens is wide spread. The kitchen cross-contamination problem may also be extended to include problems from the use of cutting boards (problematic particularly with porous material like wood) and from inadequate cooking of contaminated food. In addition, inadequate cleaning of virtually all kitchen surfaces into which human skin comes into contact, directly or indirectly, further compounds the problem of cross-contamination; and this would include not only faucet handles, but also table, counter and other surfaces, as well as handles to ovens, refrigerators, microwave units, etc.

Still another fomite is computer devices where keyboards are used by multiple users in such settings as libraries, computer labs, retail stores and offices. In fact, the Centers for Disease Control traced one norovirus outbreak to computers in a school.

Cross-contamination may also occur during travel. On public transportation such as airplanes, travelers are often provided with complimentary travel pillows. These pillows may have been used by numerous other travelers. Despite changing the outer coverings (which may not occur between flights), these pillows may still harbor pathogens spread by previous users. Similarly, headrests, armrests and cushions of airplane seats may also bear pathogens left by previous users.

While one of the present inventor's U.S. Pat. Nos. 6,468, 611 and 6,649,236 to anti-fomitic devices provided a solution to the above-mentioned problems, a need still exists for better fitting and adaptability of such anti-fomitic devices to the objects they cover.

DETAILED DESCRIPTION

Figure 1:
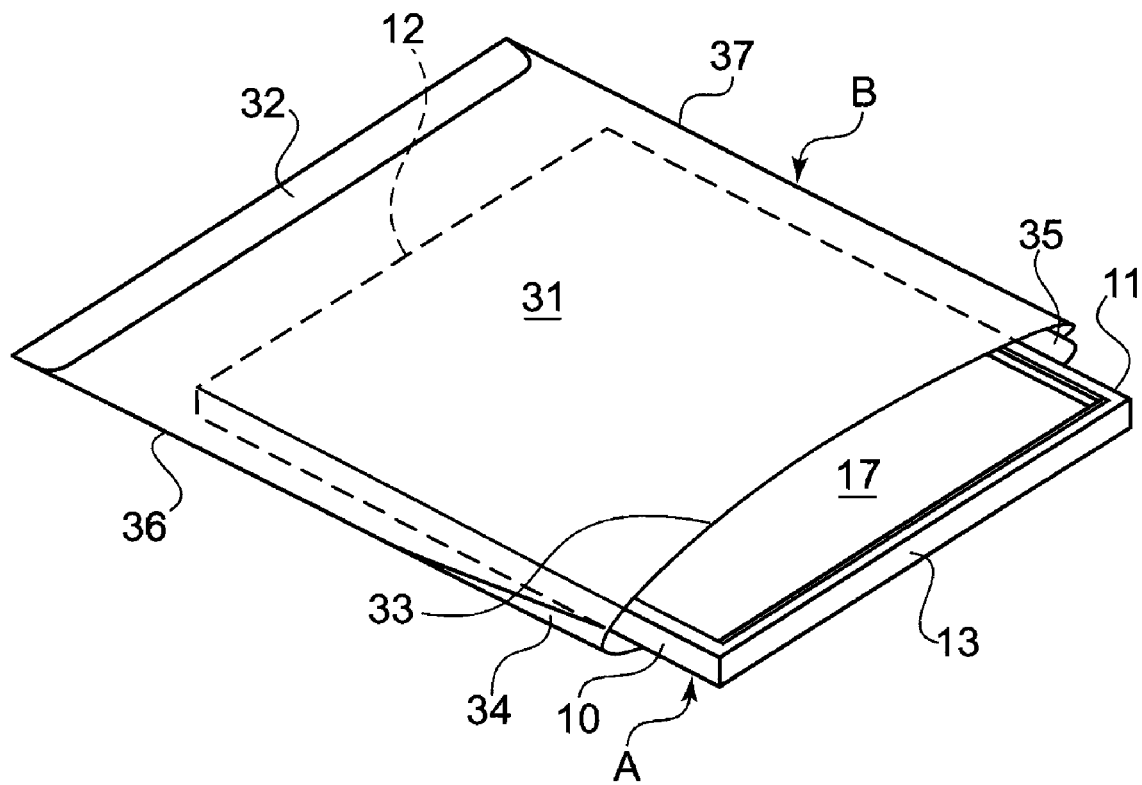
FIG. 1 illustrates a perspective view of a bag embodiment for covering an object.

Disclosed embodiments relate generally to a cover or barrier formed of shrink film to prevent cross-infection. In particular, the embodiments relate to a range of anti-fomitic covers to prevent cross-infection, including such covers for pillows, mattresses, X-ray cassettes, surgical and diagnostic equipment, toilet seats, table and chair seat surfaces, wash basin faucet handles and other handles, etc.

In the following detailed descriptions, a flat object to be covered will be designated generally as A, and the cover therefor will be designated generally as B. In general, however, object A need not be flat. A may represent any object that may be covered and that may come into contact with human skin or clothing, or A may be a body part (for example, a part covered by a diaper).

The cover B may be made of any disposable heat-shrinkable film material that is transparent to X-rays (where applicable), that is suitable for contact with human skin, and that also serves as a barrier at least to bacteria and other pathogens of a similar size. Furthermore, the barrier comprising disposable heat-shrinkable film material will prevent smaller pathogens (for example, viruses) from reaching a user.

An embodiment provides a disposable, sealable bag or envelope structure formed of heat-shrinkable film material for encasing and closely conforming to an object in a way that prevents the spread of bacteria and other pathogens among multiple persons using the same object. The object to be covered by the bag or envelope structure can be virtually any medical, surgical or diagnostic equipment item or part thereof, particularly an item or part that may come into contact with human skin or clothing, such as, for example and not as a limitation, an X-ray cassette or other X-ray recording device, a surgical instrument or diagnostic instrument, a bedding, table or chair seat surface, a faucet handle or any other handle. In addition, the object to be covered by the bag or envelope structure may be any other object that may be covered and that may come into contact with human skin or clothing, whether in a medical setting or not, such as, for example and not as a limitation, a pillow, a travel pillow, a mattress, a table, a chair, a cushion, a headrest, an armrest, a toilet seat cover, a faucet handle, or other handle. The object to be covered may also be a body part (for example, a part covered by a diaper). Collectively, the group of objects which may be covered may be referred to as "enclosed object(s)".

The enclosed objects may be found in various settings where multiple persons may come in contact with them. As an example, and not as a limitation, the enclosed objects may be in a home, in a school, in a hospital or medical setting, in an office, in a hotel, or on a public transportation vehicle such as a bus, train or airplane.

In a further embodiment, the bag or envelope structure which covers the enclosed object may be made of any disposable heat-shrinkable film material that is transparent to X-rays (where applicable), that has sufficient strength for the application, that is suitable for contact with human skin, and that also serves as a barrier at least to bacteria and other pathogens of a similar size; furthermore, smaller pathogens (for example, viruses) ideally also will not penetrate the disposable heat-shrinkable film material. As an example and not as a limitation, the heat-shrinkable film material may be PVC shrink film, polyolefin shrink film, polyester shrink film, or polyethylene shrink film. Another embodiment employs heat-shrinkable film that is biodegradable.

Referring to FIG. 1, A is featured as an X-ray cassette with sides (collectively forming a cassette frame) 10 and 11, and ends 12 and 13. The cover B of FIG. 1 has the form of a bag or envelope with a front (not shown), a back 31, sealed end edge 32, and opening 33. Cassette A is inserted into opening 33 until it is completely covered.

Another embodiment provides multiple, optional, closure/sealing methods for a disposable bag or envelope structure formed of heat-shrinkable film material for encasing and tightly conforming to an enclosed object, including but not limited to adhesive (including, for example, pressure-sensitive adhesives and adhesive strips that are covered with a protective sheet or strip when not in use), heat sealing, zippers, zip-lock structures, hook-and-loop structures (for example, Velcro®), and tucked flaps.

Referring again to FIG. 1, any of the above-listed closure mechanisms may be used to seal opening 33.

Figure 7:
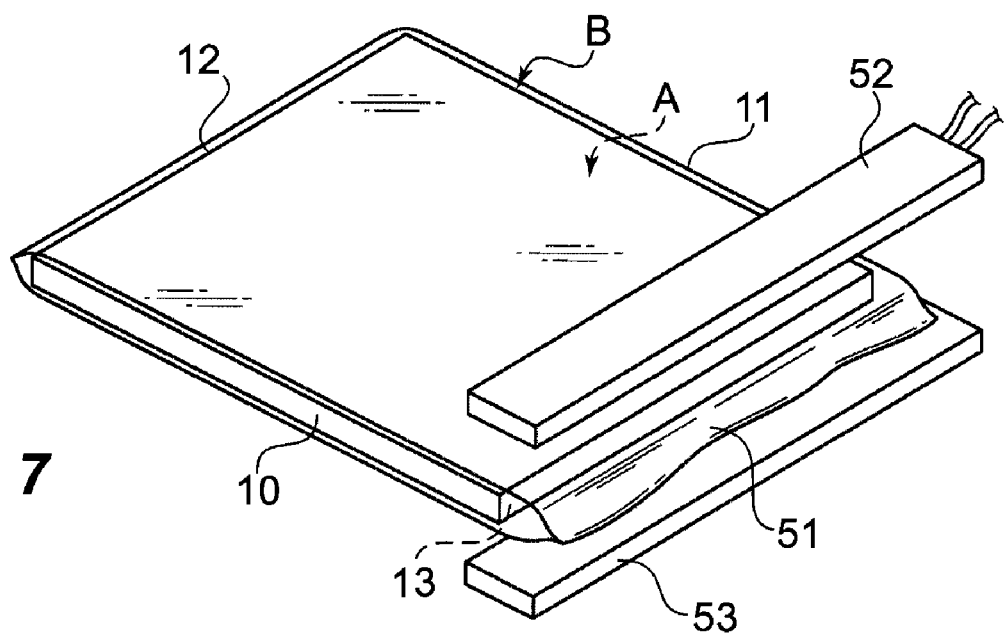
FIG. 7 illustrates a perspective view showing sealing by heat sealing.

Referring to FIG. 7, a heat sealable plastic cover/bag B encloses cassette A, and end 51 is closed is by conventional heat sealing, for example with an impulse sealer or an electrically heated anvil 52, combined with companion anvil 53. In addition, with suitable plastic, the cover can be heat shrunk about the cassette by subjecting the cover to a short blast of hot air.

Another embodiment provides a disposable, sealable bag formed of heat-shrinkable film material for encasing and closely conforming to an enclosed object, where the opening of the bag incorporates a slit at one or more edges to facilitate entry and positioning of the object therein.

Referring again to FIG. 1, the bag or cover B can optionally include slits 34 and 35 at the opening. The slits may extend about ⅓ to ½ of the way down edges 36 and 37 of the bag. The purpose of slits 34 and 35 is to facilitate insertion of the cassette A into the bag.

In another embodiment, heat may be applied in a number of ways to shrink the anti-fomitic heat-shrinkable film cover so that the film cover more closely conforms to the shape of the enclosed object. For example, where the enclosed object is in a home or hotel setting, hand-held hair dryers are frequently available and may be used to apply hot air to heat shrink the cover described above.

Figure 2A:
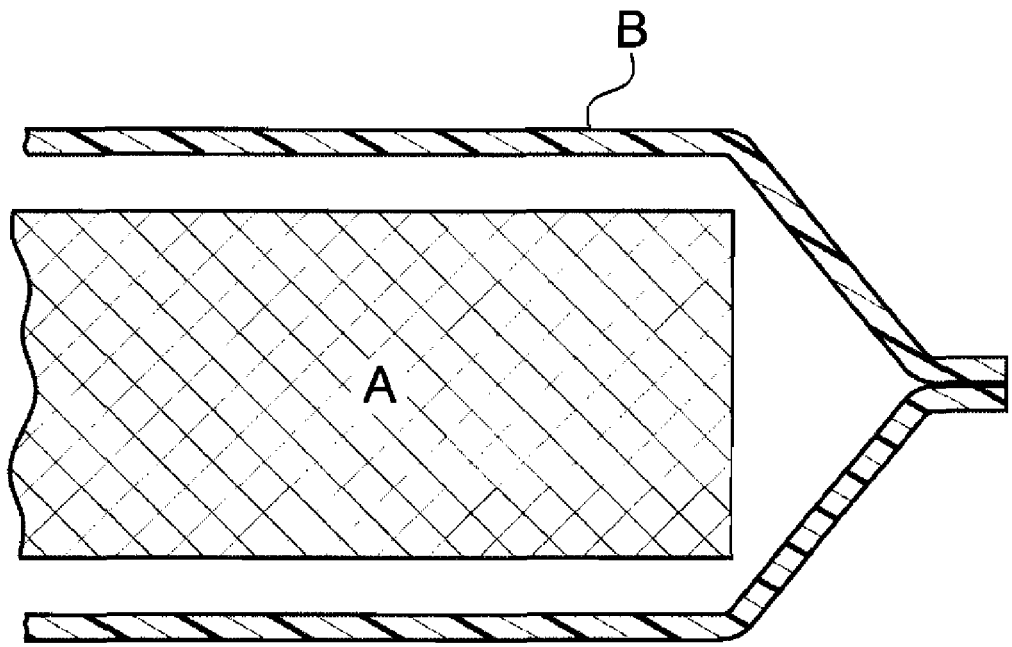
FIGS. 2A and 2B illustrate an embodiment of a barrier before and after heat shrinking.
Figure 2B:
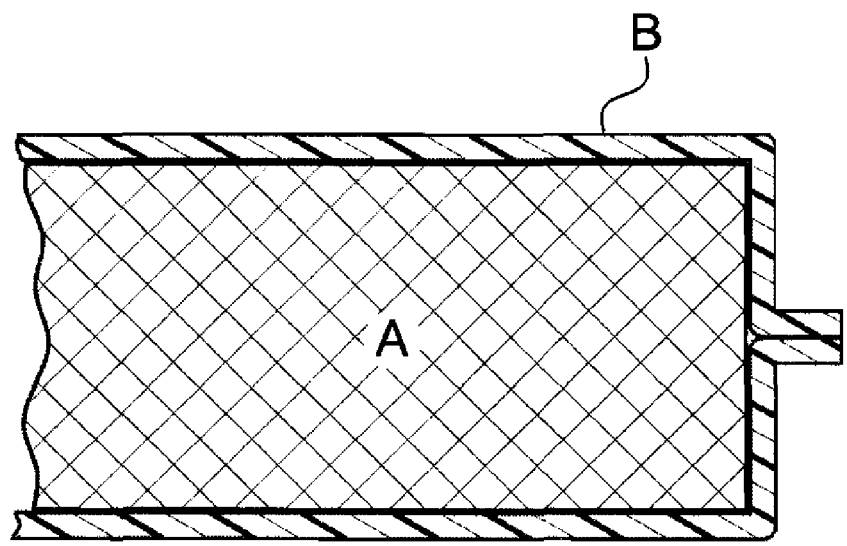

Referring to FIGS. 2A and 2B, the operation of the heat shrink film to conform to the shape of the object covered is illustrated. In FIG. 2A, an object A is enclosed in a bag or barrier B. Upon the application of heat to the barrier material that is formed from heat-shrinkable film material, the barrier B shrinks to conform to the surface of the enclosed object A, as illustrated in FIG. 2B.

A further embodiment provides a plurality of disposable covers formed of heat-shrinkable film material for covering and closely conforming to an enclosed object, where the outermost cover of the plurality of covers can be disposably removed between contact of persons to prevent cross-contamination. The exterior of the inner layers can be sterilized so that removal of each outer layer provides a new, totally clean surface.

Figure 2C:
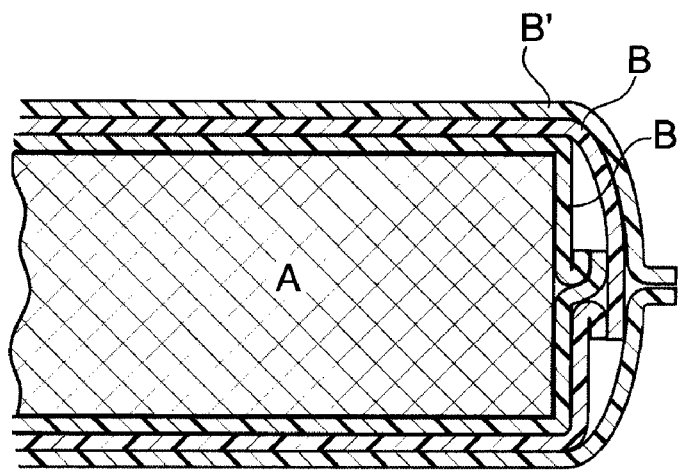
FIGS. 2C and 2D illustrate an embodiment of a barrier that incorporates a plurality of layers.
Figure 2D:
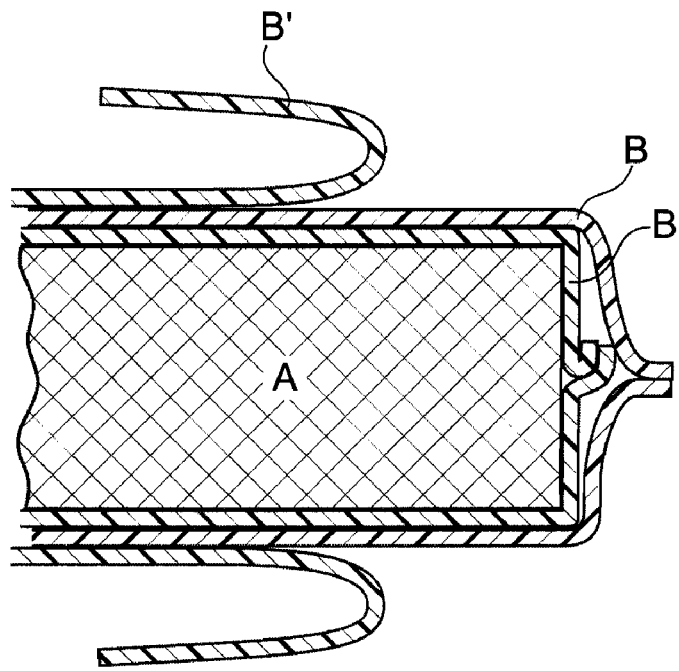
Figure 2E:
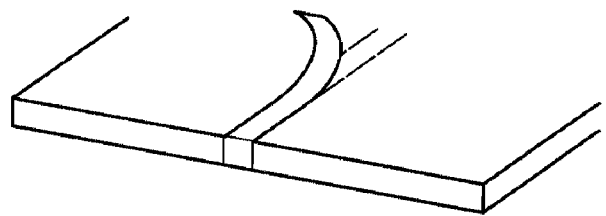
FIG. 2E illustrates an embedded strip for selective removal of these layers.

As illustrated in an embodiment in FIG. 2C, a plurality of heat-shrink film barriers B are fit around an enclosed object A. While illustrated as having three layers, the invention is not so limited and requires only two or more layers. When an outer barrier B' becomes contaminated by contact with pathogens or the like, the barrier B' can be removed, as illustrated in FIG. 2D, and disposed of prior to contact with other people to prevent cross contamination. To assist in removal of the plurality of heat-shrink film barriers B, B', each can include an embedded strip, as illustrated by an embodiment shown in FIG. 2E, with a pull handle to ease removal of the film barrier. Preferably, the outer surface of each inner barrier B is sterilized so that removal of the adjacent outer layer B' of the barrier will present a sterilized surface.

Another embodiment provides a disposable bag formed of heat-shrinkable film material for covering and tightly conforming to the front of an enclosed object by providing "end pockets" at each end of a flat sheet of shrink film material. Thus, the front surface of the object is covered, as well as the back surface at each end to the extent of the depth of the two "end pockets." The bag may be further shrunk to fit the enclosed object by the application of heat.

Figure 3:
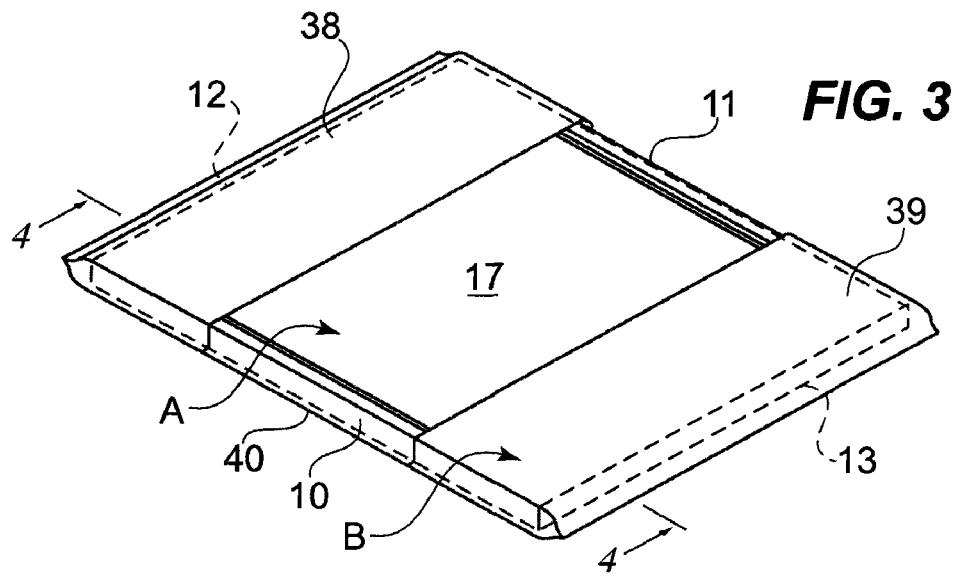
FIG. 3 illustrates a perspective view of an embodiment with an "end pocket" at each end of a sheet that covers the front surface of an object.
Figure 4:
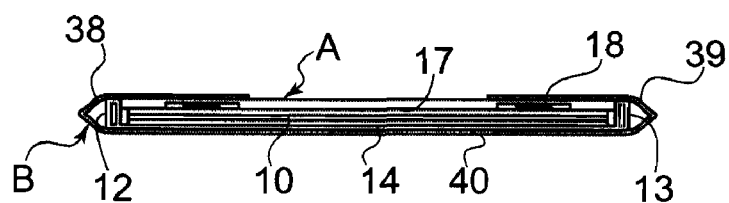
FIG. 4 illustrates a cross sectional view along line 4-4 of FIG. 3.

Referring to FIGS. 3 and 4, cover B is shown to comprise end pockets 38 and 39 and an intermediate portion 40 that covers the front surface 14 of the enclosed object A—in this illustration, an X-ray cassette. This embodiment is used by inserting cassette end 13 into end pocket 39, and cassette end 12 into end pocket 38. FIG. 4 represents the cross sectional view along line 4-4 of FIG. 3.

Another embodiment is a disposable flat sheet formed of heat-shrinkable film material with a fastening mechanism on one surface at each end, such that the object to be covered by the sheet (for example, a table or chair seat surface, etc.) is placed face down on the sheet (or vice versa) and the two ends are folded around the object such that the fastener ends of the sheet overlap and may be fastened securely to each other, thus enclosing the object snugly in the sheet. Heat may then be applied to the heat-shrinkable film material, so that the cover shrinks to conform further to the surface of the covered object.

Figure 5:
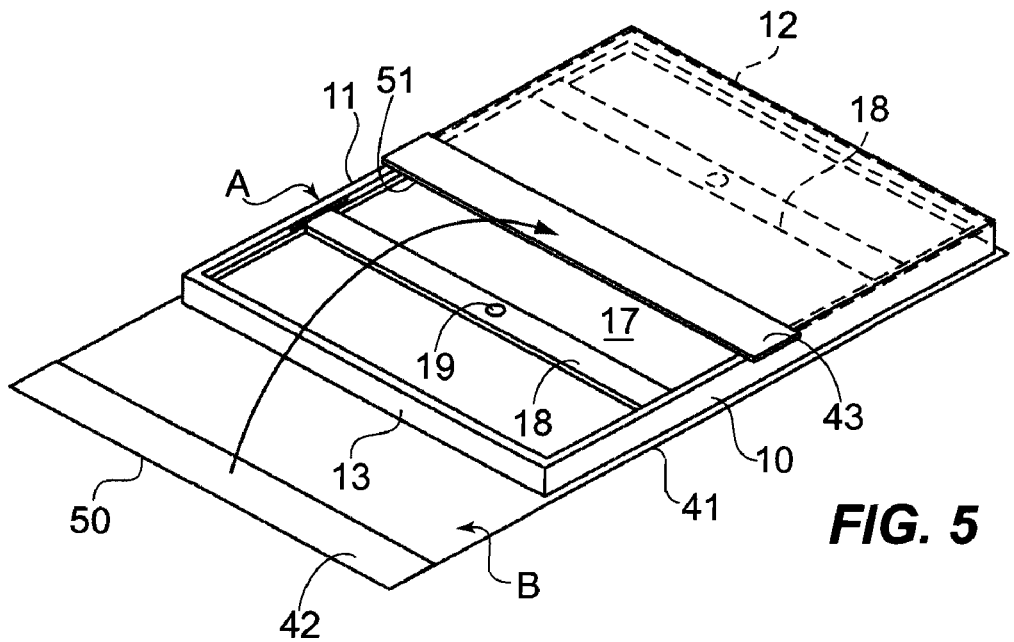
FIG. 5 illustrates a perspective view of an embodiment in which a sheet of cover material and adhesive attachment mechanism are used to cover just the front and back surfaces of an object.

Referring to FIG. 5, cover B is shown as a single sheet 41 having ends 50 and 51. The inside of end 50 is provided with a coating of pressure-sensitive adhesive 42. The outside of end 51 is also provided with pressure-sensitive adhesive 43. The length of sheet 41 is sufficient to permit mutual contact of the entire widths of adhesive strips 42 and 43 when the sheet is wrapped around the enclosed object A. Any of the other closure mechanisms enumerated above may also be used.

Another embodiment provides a disposable flat sheet formed of heat-shrinkable film material for covering the front of an enclosed object by merely folding ends over to attach by adhesive to the back of the object. Heat may then be applied to the heat-shrinkable film material, so that the cover shrinks to conform further to the surface of the enclosed object.

Figure 6:
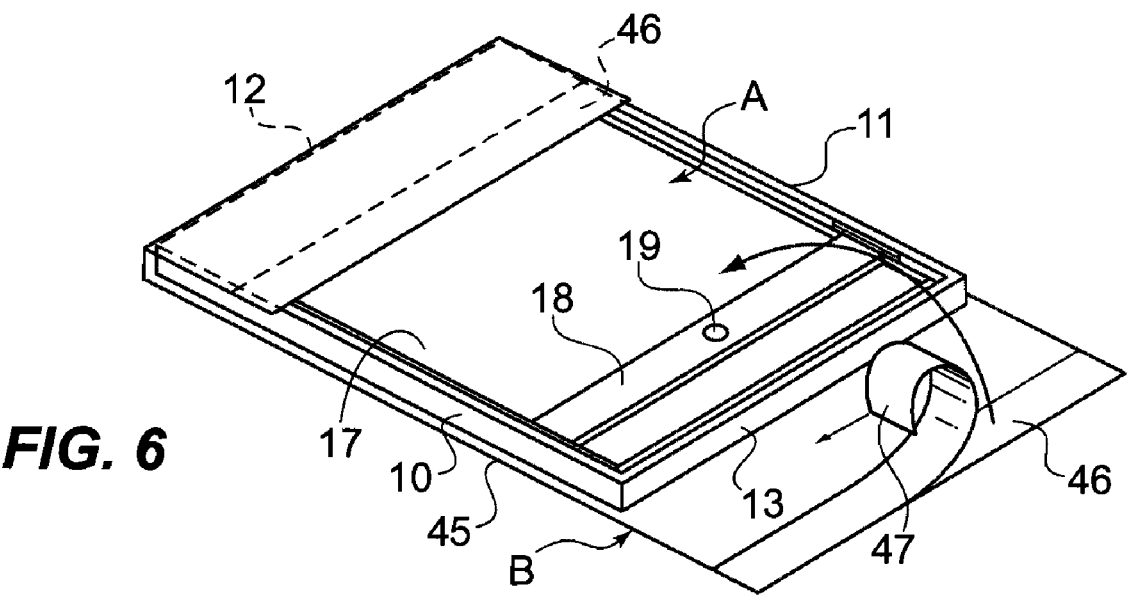
FIG. 6 illustrates a variation on the FIG. 5 embodiment in which the front of the object and the ends of the back are covered, with adhesive contacts being effected by the cover ends directly onto the back of the object.

Referring to FIG. 6, cover B is shown as a single sheet 45 that is coated with pressure-sensitive adhesive 46 at both ends, including a protective strip 47 that is removed by peeling just prior to application. In use, enclosed object A (in this illustration, an X-ray cassette) is positioned face down on the cover, protective strips 47 are removed, and the ends of sheet 45 are wrapped around to the back of the enclosed object A, where the pressure-sensitive adhesive strips 46 engage the back 17 and optionally also sides 10 and 11 of the enclosed object A.

Yet another embodiment provides a disposable bag structure formed of heat-shrinkable film material for covering and closely conforming to an enclosed object, where the disposable bag structure is part of a continuous structure of end-to-end bags that may be stored in rolled form, and with perforations or other scoring between adjacent bags to facilitate their separation when ready for use.

A further embodiment provides a disposable, sealable bag formed of heat-shrinkable film material that (prior to use) is folded back upon itself such that, once the object to be covered is inserted into the bag (and thereby is partially covered to the depth of that portion of the bag), the folded-over section is pulled over the remaining portion of the object, and closure is effected. Hence, the previously internal, sterile, folded-over bag surfaces become the external surfaces against which the skin of a person comes in contact. Such back-folded heat-shrinkable bags are intended for a broad range of applications, and may be used, for example but not as a limitation, for coverage of any of the group of enclosed objects described above.

Figure 8:
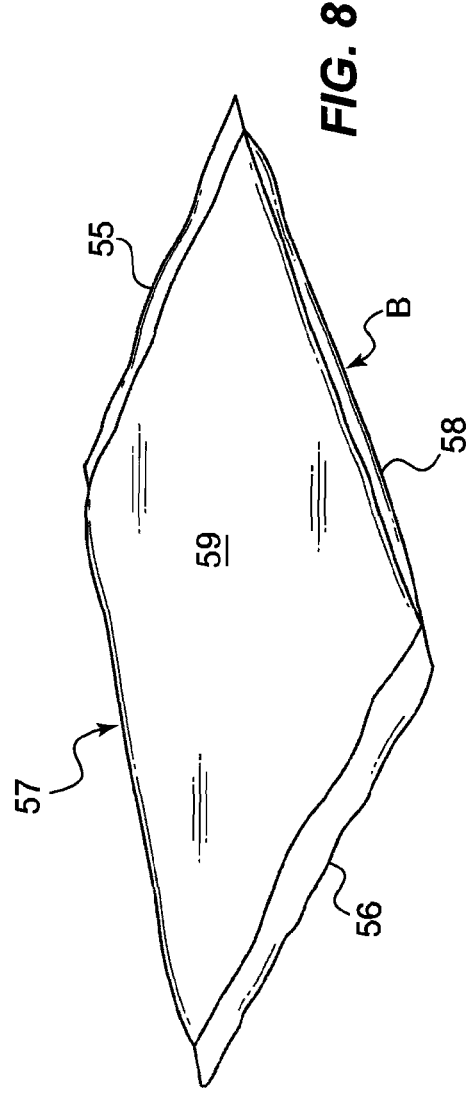
FIG. 8 illustrates a perspective view of an empty bag whose internal surfaces are sterile.
Figure 9:
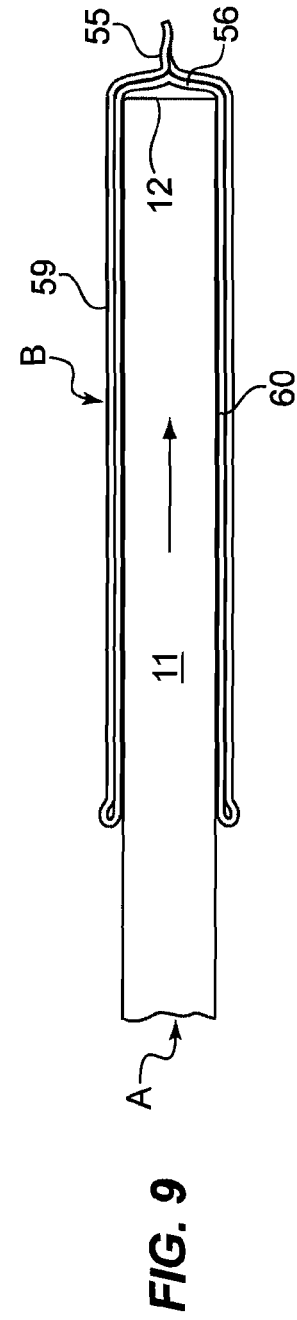
FIG. 9 illustrates a cross sectional view of the internally sterile bag of FIG. 8 folded back upon itself as an object is positioned therein by pressing against one end of the bag.
Figure 10:
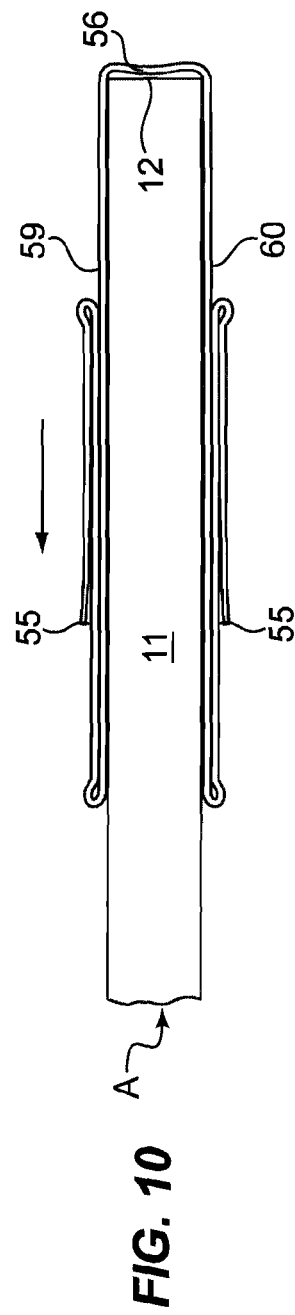
FIG. 10 illustrates the cross sectional view of FIG. 9 with an open end of the bag being advanced in a direction to unfold the bag, and to cover the uncovered end of the object positioned therein.

Referring to FIGS. 8, 9 and 10, these figures are related, and show how a cover surface that will contact a person can be kept sterile until shortly before use. A plastic bag B has ends 55 and 56, a front 59, and a rear 60. Either or both ends 55 and 56 are sealed in such a manner that, while air-tight, they can be readily opened. This can be achieved by tack sealing or incorporation of a tear strip for the opening of a conventional heat seal. The remaining edges are sealed in any conventional air-tight permanent manner. The bag is prepared under sterile conditions such that at least the interior is sterile at time of use. In addition, end-to-end such bags may be prepared and stored on rolls, with appropriate scoring or perforations between the bags.

Referring to FIGS. 8 and 9, enclosed object A (in this example, an X-ray cassette) is pressed against one end of bag B, for example end 56, and forced in such a manner that the bag doubles back on itself to the point that end 56 abuts against end 55, and edge 12 of the cassette is flush against end 56. This operation may be aided by a sleeve-like jig (not shown) that fits around the cassette. Thereafter, sealed end 55 is opened fully, and the bag is peeled back on itself, as is shown in FIG. 10. Thus, the previously sterile inside surfaces of the bag are now on the outside of the bag, ready for engagement with the skin of a medical patient and free of bacteria and pathogens that may lurk on the surfaces of the cassette.

The inside-out principle demonstrated in FIGS. 8-10 may be applied to any of the group of enclosed objects previously described.

One benefit of the inside-out principle as exemplified in FIGS. 8-10 is that bacteria and other pathogens on the skin of a person (for example, on hands holding the X-ray cassette in place, or on the skin of the body part being X-rayed) may thereby be eliminated from the cross-contamination cycle that otherwise would prevail in the clinical setting using conventional cassettes.

A further embodiment provides a disposable tube or sleeve structure formed of heat-shrinkable film material for encasing and tightly conforming to an enclosed object.

Figure 11A:
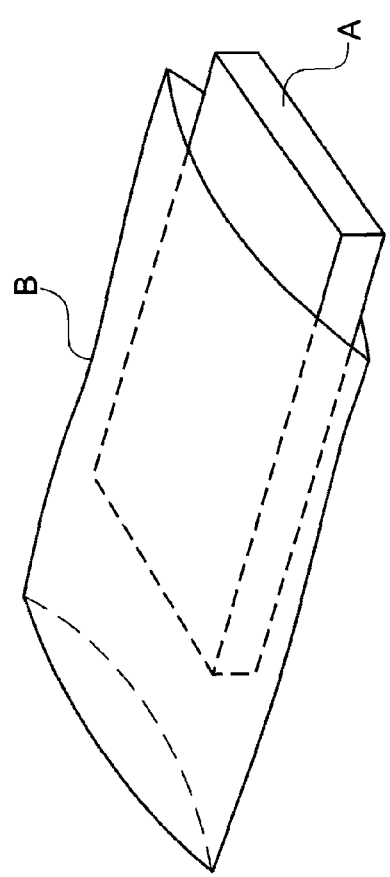
FIGS. 11A and 11B illustrate an embodiment that uses a tubular structure for the barrier.

Referring to FIG. 11A, a generally tubular structure is demonstrated which is formed of heat-shrink film material that is open at both ends, as illustrated by barrier B. The tubular barrier B can, like the bags, be produced singly or on rolls with perforations for separating adjacent sections. Also like the bags, the tubular barrier can have a sterilized interior and be inverted prior to covering an enclosed object A so as to present a sterile surface.

Figure 11B:
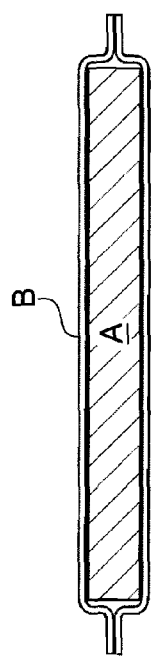

After an object A is inserted into the tubular barrier B, heat can be applied to conform the shrink film material to the surface of the object A, as illustrated in FIG. 11B. If the film shrinks sufficiently, it can shrink against itself to form a seal at each end of the tubular barrier B.

Though the heat-shrinkable anti-fomitic covers of the various embodiments are directed mainly to various medical, surgical and diagnostic apparatuses and computer keyboards, they also apply to such areas as pillows and mattresses, travel pillows, faucet handles and other handles, table and chair seat surfaces, headrests, armrests, and toilet seats. Thus, by using the back-folded bag embodiments or disposably-removable plurality of covers embodiments, a pillow cover, for example, may be made that permits a hospital patient to experience a totally clean surface on which to place his head or other body part. Alternatively, one or more of the embodiments may be used to provide a clean pillow cover for a pillow received and used during an airline flight or hotel stay. Another embodiment can be placed over a keyboard to allow heat-shrinking to fit over the keys of a computer keyboard. This shrink-fit barrier may be thrown away after each use.

The disclosed embodiments overcome limitations in the prior art by providing a cover that can conform very closely to the object being covered, yet be easily slipped over the object prior to application of heat to the heat shrink film material.

Although described herein with reference to particular embodiments, one of ordinary skill in the art will recognize that numerous additional embodiments are possible and that various modifications can be made without departing from the scope of the present invention, which is limited only by the claims below. For example, the embodiments illustrated in the drawings have emphasized use with X-ray cassettes, and in one embodiment use with pillows, mattress covers, table covers, etc. However, it is to be understood that the general concepts may be applied to a broad range of surgical or diagnostic equipment, as well as numerous domestic and household applications not specifically enumerated herein. Thus, it is intended that the specific embodiments presented herein are not limiting as to scope, but, rather, detail specific embodiments that may be generalized to a larger constellation of potential applications. Further, any reference to claim elements in the singular, for example, using the articles "a," "an," or "the" is not to be construed as limiting the element to the singular.

What is claimed is:

1. A heat-shrinkable anti-fomitic device for covering an object, consisting essentially of:
    a plurality of barriers sized to cover a surface of an object, each of the plurality of barriers having an interior surface for facing the object and an exterior surface,
    each of the plurality of barriers comprising a material that:
        serves as a barrier to pathogens, and
        is formed from a heat-shrink film material,
    wherein the plurality of barriers includes at least three barriers; and
    wherein each of the plurality of barriers is a tubular structure with a first open end and a second open end.

2. The heat-shrinkable anti-fomitic device according to claim 1, where the material that serves as a barrier to pathogens is a plastic selected from the group consisting of polyvinyl chloride, homopolymers of polyvinyl chloride, copolymers of polyvinyl chloride, polyesters, polyethylenes, polypropylenes, and polyolefins.

3. The heat-shrinkable anti-fomitic device according to claim 1, where the material that serves as a barrier to pathogens is biodegradable.

4. The heat-shrinkable anti-fomitic device according to claim 1, wherein the tubular structure further comprises a sterile interior surface, and wherein said tubular structure is turned inside out to cover the object, resulting in the sterile interior being on the outside.

5. The heat-shrinkable anti-fomitic device according to claim 1, further comprising the tubular structure being dimensioned so as to enable covering of said object where the object is selected from the group consisting of surgical devices, surgical instruments, diagnostic equipment, pillows, mattresses, faucet handles, toilet seats, table tops, and chair seats.

6. The heat-shrinkable anti-fomitic device according to claim 1, further comprising the tubular structure and at least one open end of the tubular structure being dimensioned so as to cover an object selected from the group consisting of mattresses and pillows.

7. The heat-shrinkable anti-fomitic device according to claim 1, wherein the outer surface of each of the plurality of barriers is sterilized.

8. The heat-shrinkable anti-fomitic device according to claim 1, wherein each of the plurality of barriers comprises an embedded pull strip to aid in removal of the shrink film from the object.

9. A heat-shrinkable anti-fomitic device for covering an object, consisting essentially of:
    a plurality of barriers sized to cover a surface of an object, each of the plurality of barriers having an interior surface for facing the object and an exterior surface,
    each of the plurality of barriers comprising a material that:
        serves as a barrier to pathogens, and
        is formed from a heat-shrink film material,
    wherein the plurality of barriers includes at least three barriers; and
    wherein each of the plurality of barriers comprises a sheet of heat-shrink film material sized to wrap around an object.

10. The heat-shrinkable anti-fomitic device according to claim 9, wherein the sheet of heat-shrink film material shrinks to conform further to the object when heat is applied.

11. A heat-shrinkable anti-fomitic device for covering an object, consisting essentially of:
    a plurality of barriers sized to cover a surface of an object, each of the plurality of barriers having an interior surface for facing the object and an exterior surface, each of the plurality of barriers comprising a material that:
  serves as a barrier to pathogens, and
  is formed from a heat-shrink film material,
wherein the plurality of barriers includes at least three barriers; and
wherein each of the plurality of barriers is a disposable flat sheet for covering the front of an object.

12. The heat-shrinkable anti-fomitic device according to claim 11, wherein each disposable flat sheet of the plurality of barriers comprises an embedded pull strip to aid in removal of the sheet from an object.

* * * * *